US006590113B1

(12) United States Patent
Sleeter

(10) Patent No.: US 6,590,113 B1
(45) Date of Patent: Jul. 8, 2003

(54) PROCESS FOR TREATING OILS CONTAINING ANTIOXIDANT COMPOUNDS

(76) Inventor: Ronald T. Sleeter, 1263 Semor Dr., Decatur, IL (US) 62521

( * ) Notice: Subject to any disclaimer, the term of this patent is extended or adjusted under 35 U.S.C. 154(b) by 0 days.

(21) Appl. No.: 10/106,614

(22) Filed: Mar. 26, 2002

(51) Int. Cl.[7] ........................................ C07C 53/00
(52) U.S. Cl. ........................................ 554/1
(58) Field of Search ........................................ 554/4

(56) References Cited

U.S. PATENT DOCUMENTS 4,789,554 A 12/1988 Scavone et al.

OTHER PUBLICATIONS

De Greyt, Wim F.; Kellens, Marc J.; Huyghebaert, Andre D.: "Effect of physical refining on selected minor components in vegetable oils," Fett/Lipid 101 (1999), Nr. 11, pp. 428–432.

Parkhurst, R.M.; Skinner, W.A.; Strum, Priscilla A.: "The Effect of Various Concentrations of Tocopherols and Tolopherol Mixtures on the Oxidative Stability of A Sample of Lard," Journal of the American Oil Chemists Society, vol. 45, 641–642 (1968).

Marcuse , R.; Fredriksson, P.O.: "Fat Oxidation at Low Oxygen Pressure: II Kinetic Studies on Linoleic Acid Oxidation in Emulsions in the Presence of Antioxidants," Journal of the American Oil Chemists Society, vol. 46, 262–268 (May 1969).

Stern, Max H.; Robeson, Charles D.; Weisler, Leonard; Baxter, James G.: "δ–Tocopherol I, Isolation from Soybean Oil and Properties," Journal of the American Chemical Society, vol. 69, 869–874 (Apr. 1947).

Durckheimer, Walter; Cohen, Louis A. : "The Chemistry of 9–Hydroxy–α–tocopherone, a Quinone Hemiacetal," (Oct. 20, 1964).

Van Dalen, J.P.; Van Putte, K.P.A..M. : "Adsorptive Refining of Liquid Vegetable Oils," Fat Sci. Technol., vol. 94, pp 567–570 (Dec. 1992).

Lehman, Robert W. : "Vitamin E—Chemistry And Analysis," (Aug. 1969).

"Handbook of Coatings Additives," edited by Leonard J. Calbo, Marcell Dekker, Inc., New York and Basel, 1987, p. 490–92.

*Primary Examiner*—Deborah D. Carr
(74) *Attorney, Agent, or Firm*—Lathrop & Gage LC

(57) ABSTRACT

A process for treating a first oil containing antioxidant compounds selected from tocopherols, tocotrienols, sterols, or mixtures thereof comprising contacting the first oil with an effective amount of at least one compound under suitable reaction conditions to esterify at least about 50% of the antioxidant compounds to produce a second oil containing esters of the antioxidant compounds, the second oil and oil-based coatings or inks produced therefrom having reduced yellowing and improved drying property.

74 Claims, No Drawings

PROCESS FOR TREATING OILS CONTAINING ANTIOXIDANT COMPOUNDS

BACKGROUND OF THE INVENTION

This invention relates to a process for treating oils containing antioxidant compounds containing free hydroxyl groups to form esters of the antioxidant compounds. This invention also relates to a process for treating triglyceride based oils to reduce yellowing of the oils, and oil-based coatings or inks. This invention further relates to a process for treating triglyceride based oils to improve the drying time of the oils, and oil-based coatings or inks. This invention further relates to a process for recovering esters of antioxidant compounds from treated oils.

For as long as triglyceride oils have been used either as triglycerides or modified for coatings such as alkyd based paints, yellowing has been a significant problem and has hindered their effective use or limited their applications. Due to cost and availability, linseed oil in particular has been an oil of choice for coatings, but significantly suffers from this problem. Additionally, the dry time has been a problem due to the presence of tocopherols, which are antioxidants and act as a brake to slow drying. Processing steps to improve dry times generally include blowing or heat bodying the oils or, more recently, conjugation of oils. Tung oil generally dries in a reasonable time and yellows to a lesser extent, but is costly. It is well known that a major contribution to the browning of oils results from the tocopherols present, which, when oxidized, impart a significant brown color. One such oxidization reaction product is known as toco red.

Frying fats are generally stripped by high temperature deodorization to reduce the amount of tocopherols to a minimum in order to improve fry life (U.S. Pat. No. 4,789,554, Scavone et al., "High Temperature Vacuum Steam Distillation Process to Purify and Increase the Fry Life of Edible Oils"). Fry life is determined by the increased browning of the oil until it reaches a quality control maximum, at which point the frying oil is discarded. After tocopherol stripping this browning is significantly reduced and apparent fry life can thus be increased. The paper "Effect of physical refining on selected minor components in vegetable oils", by Wim F. De Greyt, Marc J. Kellens and Andre D. Huyghebaert, Fett/Lipid 101 (1999), Nr. 11, pp. 428–432 ("De Greyt, et al."), discloses that deodorization can be used to reduce the level of tocopherols in refined soybean oil from approximately 900–1400 ppm to approximately 500 ppm while maintaining the optimum oxidative stability of the soybean oil. Tocopherols slow the dry time as discussed above. In the book, "Handbook of Coatings Additives" edited by Leonard J. Calbo, Marcell Dekker, Inc., New York, Publisher, 1987, page 490 it is disclosed that "[t]he drying of unsaturated oil films is the result of autoxidation. Drying by autoxidation is a very interesting and useful process. Once a film has been cast, all that is required for the drying to occur is the absorption of oxygen from the air. Like oils, alkyds containing unsaturated side chains dry as a result of the autoxidation process. The stages of drying include an initial quiescent period where the film appears dormant. This is generally attributed to the presence of antioxidants in the oil. The next steps are oxygen absorption, peroxide formation, and peroxide decomposition resulting in the generation of free radicals . . . ". The free radicals generate and propagate chain reactions, which accelerate drying. The quiescent period referred to above, which is due to antioxidants in the oil, is a direct result of the tocopherols, since these are the major antioxidants present.

The antioxidant activity of tocopherols in oils has been known for a long time. In "The Effects of Various Concentrations of Tocopherols and Tocopherol Mixtures on the Oxidative Stability of a Sample of Lard", by R. M. Parkhurst, W. A. Skinner and Priscilla Sturm, Journal of the American Oil Chemists Society 45, 641–642 (1968) and "Fat Oxidation at Low Oxygen Pressure: II Kinetic Studies on Linoleic Acid Oxidation in Emulsions in the Presence of Antioxidants", by R. Marcuse and P. O. Fredriksson, Journal of the American Oil Chemists Society 46, 262–268 (1969) disclose that significant increase in induction time (the period of quiescence) occurs when tocopherols are added to oils, which have been totally stripped. Tocopherols inhibit oxidation by terminating free radical propagation. The induction time, then, is the period when the tocopherols are being oxidized, while terminating this free radical oxidation.

It is currently known in the art to reduce the level of tocopherols in oils by utilizing: (1) removal by high vacuum steam stripping at elevated temperature, commonly referred to as deodorization (a process known as physical refining utilizes similar techniques, namely vacuum stripping of free fatty acids), (2) molecular distillation (also, now utilizing short path high vacuum distillation technology), and (3) adsorption with the use of powdered or granular carbon, which can selectively adsorb a portion of the tocopherols present. A reference with conditions for the use of molecular distillation to recover tocopherols from oils is given by Max Stern, C. D. Robeson, L. Weisler and J. C. Baxter in Journal of the American Chemical Society 69, 869–874 (1947), "gamma-tocopherol I, Isolations from Soybean Oil and Properties". The conditions used were a centrifugal type molecular still at 240□C and 0.004 mm Hg. Carbon adsorption of tocopherols is known generally in the art but is not widely used because it is too costly and inefficient, and companies that employ such techniques hold their procedures proprietary.

Most triglyceride oils, including linseed oil, contain trace amounts of free fatty acids. Two primary means of removing these free fatty acids are caustic refining and physical refining. Most oils, including linseed oil, are generally caustic refined to remove these trace amounts of free fatty acids. This process is described in "Bailey's Industrial Oil and Fat Products, Vol. 2, Fourth Ed., edited by Daniel Swern, John Wiley and Sons publishers, 1982, pp. 268–288. It should be noted that prior to refining, oils are generally subjected to removal of phosphatides by employing the process known as degumming. The crude oil is mixed with hot water. Often phosphoric acid is added to acidify non-hydratable phosphatides. After a period of contact the phosphatide gums are separated by centrifugation. Following degumming, the caustic refining process involves the addition of an alkali solution of water to the oil with heat to form soaps of free fatty acids by allowing a short residence time to insure complete soap formation. The soaps are then subsequently removed by centrifuges followed by washing steps. Caustic refining is optimally used when the free fatty acid content is low.

Physical refining of oils is used primarily for triglyceride oils, such as palm oil, which contain large quantities of free fatty acids and low levels of phosphatides. For palm oils and other oils having high amounts of free fatty acids, caustic refining results in large losses of neutral oil. Thus physical, or vacuum/steam, refining is preferred. A review of the effect of physical refining is given in De Greyt, et al. De Greyt, et al. described conditions with steam rate, vacuum, temperature and time. De Greyt, et al. focused on tocopherols content and discussed their retention and effect in the physically refined oil products. The vacuum, steam and temperature involved generally do not remove a significant amount of the tocopherols from the oil.

It is desirable to provide an improved process for treating oils that reduce yellowing and drying time of the oils but which does not require the removal of antioxidant compounds containing free hydroxyl groups, e.g. tocopherols. It is also desirable to provide an improved process that permits the facile stripping of esters of antioxidant compounds containing free hydroxyl groups, e.g. tocopherols, from treated oils when needed.

SUMMARY OF THE INVENTION

According to the invention, a process for treating a first oil containing antioxidant compounds selected from tocopherols, tocotrienols, sterols, or mixtures thereof is provided which comprises contacting the first oil with an effective amount of at least one compound under suitable reaction conditions to esterify at least about 50% of the antioxidant compounds to produce a second oil containing esters of the antioxidant compounds.

In one embodiment, the second oil is optionally further treated using one or more of treatments selected from the group consisting of stripping/deodorization, carbon treating (i.e. carbon adsorption), and bleaching to produce a third oil stripped of the esters of tocopherols, tocotrienols, and sterols. In another embodiment, the third oil is optionally subjected to a further processing step selected from blowing, heat bodying, oxidation, conjugation, epoxidation, peroxidation, hydroxylation, hydroformylation, ozonolysis, chemical modification, interesterification, or complexation. It should be noted that the second oil may alternatively be subjected to those chemical reactions which do not destroy the esters thereby allowing the tocopherol, tocotrienol, and sterol esters to remain unchanged. These reactions include conjugation, blowing, heat bodying, oxidation, epoxidation, peroxidation, chemical modification, and enzyme interesterification. Enzyme interesterification would not react with the tocopherols to darken the oil and the product would be a different ester allowing for a neutral exchange. In a further embodiment, the second oil is optionally washed with water or a mild aqueous base to remove excess esterification reagents or by-products of the esterification reactions.

Further according to the invention, a process for treating a first oil containing antioxidant compounds selected from tocopherols, tocotrienols, sterols, or mixtures thereof is provided which comprises (a) contacting the first oil with an effective amount of at least one compound under suitable reaction conditions to esterify at least about 50% of said antioxidant compounds to produce a second oil containing esters of the antioxidant compounds; and (b) stripping/deodorizing the second oil to remove the esters of the antioxidant compounds and produce a third oil.

In one embodiment, esters of said antioxidant compounds removed by stripping/deodorization are recovered for direct use or further processing. In an alternative embodiment, the second oil is treated by adsorptive refining followed by physical refining. In a further embodiment, the process optionally further comprises interesterifying the third oil in the presence of a base or acid catalyst, preferably a base catalyst, to produce a product selected from interesterified oils, or esters or partial esters of fatty acids. In yet a still further embodiment, the second oil or the third oil is optionally washed with water or a mild aqueous base.

Still further according to the invention, oils prepared by the processes of the invention are provided.

BRIEF DESCRIPTION OF THE DRAWINGS

NOT APPLICABLE.

DETAILED DESCRIPTION OF THE INVENTION

A first embodiment of the invention relates to a process for treating a first oil containing antioxidant compounds having free hydroxyl groups, the antioxidant compounds being selected from tocopherols, tocotrienols, sterols, or mixtures thereof comprising contacting the first oil with an effective amount of at least one compound under suitable reaction conditions to esterify at least about 50%, of the antioxidant compounds to produce a second oil containing esters of the antioxidant compounds.

Preferably at least about 75%, more preferably at least about 90%, and most preferably at least about 95%, of the antioxidant compounds are esterified in the process of the invention.

Examples of sterols include, but are not limited to, beta-sitosterol, stigmasterol, campesterol, delta 5-avenasterol, delta 7-stigmasterol, cycloartenol, fucosterol, oryzanol, obtusifoliol, gramisterol, citrostadienol, methylenecycloartenol, beta-amyrin, cycloartanol, sesamol, brassicasterol, and other naturally occurring sterols found in natural triglyceride oils.

The concentration of antioxidant compounds having free hydroxyl groups in the first oil is known to those of ordinary skill in the art, and will vary depending on the specific first oil used. For example, typical tocopherol content of various triglyceride oils is as follows: soybean oil (250–1639 ppm), corn oil (603–1175 ppm), cottonseed oil (830–900 ppm), palm oil (360–560 ppm), rapeseed oil (690 ppm), sunflower oil (1243–2271 ppm), linseed oil (123–427 ppm), peanut oil (200–600 ppm), and olive oil (30–300 ppm). (See Untersuchungen zur Stabilitat des Tocopherolgehaltes pflanzlicher Ole, by Von Ursula Coors and A. Montag, Fett. Sci. Technol. 90, Nr. 4, 129–136 (1988); Bailey's Industrial Oil and Fat Products, Volume 1, ed. Daniel Swem, Wiley Interscience (1979); and DeGreyt, et al.).

Suitable first oils for use in the process(es) of the invention include any oil containing antioxidant compounds having free hydroxyl groups. The first oils can be selected from crude oils, degummed oils, or refined oils. The choice of crude oils, degummed oils, or refined oils will depend on the specific oil being treated according to the process(es) of the invention.

In the case of crude triglyceride oils, such as linseed oil, with low free fatty acids and high levels of phosphatides, a degumming procedure should be used prior to the esterification process of the invention. Linseed oil is first generally degummed producing raw or degummed linseed oil. This oil generally contains residual phosphatides amounting to about 100 ppm phosphorous content. The phosphorous content must be reduced to less than approximately 5 ppm. Following degumming, two options may be selected. The first option, typically used with low fatty acid containing oils, would be to caustic refine. A second option that can be considered would allow for efficient stripping of tocopherol esters by combining two processing steps of refining and stripping/deodorization. Thus, following degumming a second option would be to reduce the phosphatides by adsorptive refining with silica hydrogels. This can be accomplished by adsorptive refining with silica hydrogels or precipitated silica which is well known in the art. A paper by J. P. van Dalen and K. P. A. M. van Putte, "Adsorptive Refining of Liquid Vegetable Oils", in Fat Sci. Technol. 94 567–570 (1992) describes the process. The oil is heated, followed by the addition of citric acid solution. After a period of stirring, water is added and stirring continued. A silica hydrogel is added and stirred for a period, followed by a drying step under vacuum. A bleaching step may be incorporated with the hydrogel or followed subsequently, were approximately <1% bleaching earth is added. A vacuum is applied to reduce water content to a minimum. After filtration of the oil, esterification of the antioxidant compounds, e.g. tocopherols, can proceed according to the process(es) of the invention. This may be accomplished by contacting a reactive carboxylic acid, carboxylic acid anhydride, or acyl halide with the adsorptive refined linseed oil and holding a period of time at a temperature necessary to form the esters, e.g. tocopherol esters.

Following esterification according to the process of the invention, the oil may be subjected to stripping/deodorization to remove trace free fatty acids and the esterified tocopherols, tocotrienols, and sterols.

If the first option using caustic refining following degumming is utilized, the degummed oil would be caustic refined and water washed to remove free fatty acids and trace residual phosphatides. A bleaching step can optionally be conducted at that point. The esterification according to the invention would optimally be conducted following these operations. The resultant oil can then be used as a final product or can, optionally, be further processed to remove the esters of the tocopherols, tocotrienols, and sterols using a stripper/deodorizer. That stripped/deodorized product can then be optionally further treated by using a treatment process including conjugation, blowing, heat bodying, oxidation, epoxidation, peroxidation, chemical modification, enzyme interesterification, and the like.

The preferred first oils are triglyceride based oils including, but not limited to, triglyceride oils, modified triglyceride oils, enzyme interesterified oils, mild base catalyzed interesterified oils, high pressure interesterified oils, chemically treated or reacted oils, enzyme, mild base catalyzed or high pressure interesterified monoglycerides and/or diglycerides, diols and/or polyols, and mixtures thereof. The mild base catalyzed interesterification and high pressure interesterification are preferably conducted at low temperatures.

As used herein, interesterification is an art recognized term having the same meaning as transesterification. Therefore, an interesterified compound is a compound that has been transesterified. Interesterification is well known in the art, and the interesterification of the treated oils of the invention can be conducted using conventional methods.

Examples of suitable triglyceride oils include, but are not limited to, linseed oil, menhaden oil, soybean oil, tung oil, oiticica oil, sunflower oil, corn oil, rapeseed oil, cottonseed oil, peanut oil, olive oil, rice bran oil, wheat germ oil, canola oil, hydrogenated and partially hydrogenated oils, palm oil, palm kernel oil, coconut oil, oils from genetically modified seeds, or mixtures thereof.

Examples of modified triglyceride oils are triglyceride oils that have been subjected to modification, and include, but are not limited to, conjugated oils, blown oils, heat bodied oils, enzyme interesterified oils, mild base catalyzed interesterified oils, high pressure interesterified oils, or chemically modified oils. Chemically modified oils include, but are not limited to, triglyceride oils that have been subjected to reactions such as saponification, hydrogenation, isomerization, oxidation, peroxidation, and the like. The processes of producing conjugated oils, blown oils, heat bodied oils, and chemically modified oils are conventional processes well known to those of ordinary skill in the art.

In one embodiment, the first oil is contacted with an acyl halide. The acyl halide can either be contacted directly with the first oil or formed in situ. The acyl halide can be formed in situ by (1) contacting the first oil with an inorganic acid halide selected from $SOX_2$, $PX_3$ or $PX_5$ wherein X is selected from Cl or Br, provided the first oil contains an amount of free carboxylic acid sufficient to react with the inorganic acid halide, or (2) contacting the first oil with an inorganic acid halide and a $C_2$–$C_{24}$ carboxylic acid, including both monobasic and dibasic acids. Where $PX_3$ or $PX_5$ are used as the inorganic acid halide, it is preferred that the carboxylic acid is an aromatic carboxylic acid.

Suitable acyl halides for use in the process(es) of the invention are represented by the formula:

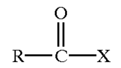

wherein R is selected from $C_1$–$C_{23}$ alkyl, or phenyl, and R is optionally substituted with at least one Cl or Br group; and wherein X is selected from Cl or Br.

Acyl halides for use in the process(es) of the invention include acyl chlorides, acyl bromides, and mixtures thereof, with acyl chlorides being currently preferred. Examples of suitable acyl halides include, but are not limited to, acetyl chloride, acetyl bromide, benzoyl chloride, benzoyl bromide, trichloroacetyl chloride, propionyl chloride, hexanoyl chloride, myristoyl chloride, stearoyl chloride, acyl chlorides of other fatty acids, and mixtures thereof.

Acyl halides may be added neat or in an organic solvent, e.g. hexane. For example, acetyl chloride may be added as a neat liquid provided the first oil is stirred sufficiently and the temperature of the first oil is low enough to allow the reaction to proceed in an efficient manner. Alternatively, acyl halides may be added by employing a gas stream fitted with a gas dispersion tube in the oil to allow for the dispersion of fine gas bubbles. The acyl halide is placed in a separate vessel and a gas (air or nitrogen, etc.) is allowed to carry volatilized acyl halide into the oil with stirring. Addition may be controlled by the amount of heat applied to the acyl halide and the gas flow rate.

Examples of suitable carboxylic acids for use in preparing acyl halides include, but are not limited to, acetic acid, trichloracetic acid, propionic acid, butyric acid, lauric acid, palmitic acid, myristic acid, stearic acid, linoleic acid, linolenic acid, oleic acid, succinic acid, maleic acid, malonic acid, adipic acid, benzoic acid, and mixtures thereof.

The temperature of the esterification reaction using acyl halides can be any suitable temperature, preferably below the boiling point of the acyl halide used in the process of the invention at the pressure used for the esterification reaction. Examples of boiling points of acyl halides include acetyl chloride (51–52° C. at 760 mm Hg), acetyl bromide (76–77° C. at 760 mm Hg), and palmitoyl chloride (194° C. at 100 mm Hg). For example, a temperature of about 10° C. to about 150° C., preferably about 20° C. to about 120° C., can be used. When the acyl halide is produced in situ by reaction with thionyl halide, it is preferred to maintain the reaction temperature below the boiling point of the thionyl halide at the pressure used for the esterification reaction. For example, the boiling point of thionyl chloride is 76° C. at 760 mm Hg. The reaction time of the esterification reaction is selected to be a time that is sufficient to esterify the desired amount of the antioxidant compounds present in the first oil.

In another embodiment, the first oil is contacted with a reactive carboxylic acid. As used herein, reactive carboxylic acid means a $C_1$–$C_6$ aliphatic (preferably $C_1$–$C_3$ aliphatic) carboxylic acid, optionally halo-substituted, such as with Cl or Br, and any aromatic carboxylic acid whose reactivity is great enough to produce the esters of the invention. Examples of suitable reactive carboxylic acids include, but are not limited to, formic acid, acetic acid, trichloracetic acid, propionic acid, hexanoic acid, and mixtures thereof. The currently preferred reactive carboxylic acids are formic acid and acetic acid.

The temperature of the esterification reaction using reactive carboxylic acids can be any suitable temperature, preferably below the boiling point of the reactive carboxylic acid used in the process of the invention at the pressure used for the esterification reaction. For example, a temperature of about 100° C. and greater, preferably about 100° C. to about 140° C., can be used. A temperature greater than 100° C. allows for water vapor to be removed from the reaction mixture under atmospheric pressure conditions, thereby driving the esterification reaction to completion. The reaction time of the esterification reaction is selected to be a time that is sufficient to esterify the desired amount of the antioxidant compounds present in the first oil.

In a further embodiment, the first oil is contacted with a carboxylic acid anhydride. In one preferred embodiment, the anhydride is soluble in the first oil. In another preferred embodiment, while acetic anhydride is not soluble, it is preferred to use acetic anhydride if subsequent stripping of the esters is to be done. Examples of suitable carboxylic acid anhydrides includes, but are not limited to, maleic anhydride, acetic anhydride, propionic anhydride, benzoic anhydride, and mixtures thereof.

The temperature of the esterification reaction using carboxylic acid anhydrides can be any suitable temperature, preferably below the boiling point of the carboxylic acid anhydride used in the process of the invention at the pressure used for the esterification reaction. For example, a temperature of about 100° C. and greater, preferably about 100° C. to about 140° C., can be used. The reaction time of the esterification reaction is selected to be a time that is sufficient to esterify the desired amount of the antioxidant compounds present in the first oil.

If an oil produced by the process(es) of the invention is required to be an edible oil product, acetate or fatty acid esters of the antioxidant compounds are preferred unless the esters of the antioxidant compounds are to be removed from the oil after esterification has occurred.

The amount of acyl halide, carboxylic acid anhydride, or reactive carboxylic acid needed to esterify the antioxidant compounds will depend on the amount of antioxidant compounds present in the first oil as well as the amount of any other compounds containing free hydroxyl groups, e.g. trace long chain alcohols, decomposition products from oil oxidation, etc. In addition, any trace water present in the first oil may also be reactive with the esterifying compounds and will impact the amount of esterifying compound required. The amount of acyl halide, carboxylic acid anhydride, or reactive carboxylic acid contacted with the first oil can be expressed as a ratio of the equivalents of the compound to esterify the antioxidant compounds to the equivalents of hydroxyl groups in the antioxidant compounds. Generally, the ratio of the equivalents of the compound to esterify the antioxidant compounds to the equivalents of hydroxyl groups in the antioxidant compounds is about 1:1 to about 10:1, preferably about 1.1:1 to about 2:1.

A second embodiment of the invention relates to a process for treating a first oil containing antioxidant compounds selected from tocopherols, tocotrienols, sterols, or mixtures thereof comprising (a) contacting the first oil with an effective amount of at least one compound under suitable reaction conditions to esterify at least about 50% of the antioxidant compounds to produce a second oil containing esters of the antioxidant compounds; and (b) stripping/deodorizing the second oil to remove the esters of the antioxidant compounds and produce a third oil.

In another embodiment, the second oil is treated by adsorptive refining and followed by a subsequent physical refining treatment to produce a third oil.

For triglyceride oils, e.g. linseed oil, where the product will be used for industrial products where tocopherols are detrimental, or for oils further processed by interesterification, advantage is taken by employing the use of stripping/deodorization for the facile removal of volatile esters, e.g. tocopherol esters, produced in the process of the invention.

If removal of the esters, e.g. tocopherol esters, following esterification is desired, the second oil is subjected to the conventional conditions of stripping/deodorization, e.g. high vacuum and steam, to easily strip the esters, e.g. tocopherol esters, from the second oil. The distillate may then be subjected to conventional purification methods to recover and isolate the esters, e.g. tocopherol esters, for value added uses. Typical stripper/deodorizers are described in the Scavone, et al. patent and De Greyt, et al. paper cited above. In general, these are columns filled with structured packing or are shallow bed deodorizers. These are heated to high temperatures under vacuum, and a stripper gas, such as steam or nitrogen, is used to facilitate removal of volatiles. If recovery of the esters for value added uses is desired, a preferred embodiment is to conduct the stripping/deodorization in two stages wherein the second oil is first deodorized to remove free fatty acids, and then subsequently stripped to recover a distillate stream containing the esters.

In cases where tocopherol, tocotrienol, and sterol stripping is warranted, such as in preparation for subsequent base or acid catalyzed interesterification using a suitable base or acid catalyst, it is advisable to strip the esters prior to the interesterification reaction. Interesterification is preferably catalyzed by bases, such as sodium methoxide and the like. This reaction further generally causes darkening of the oil if antioxidant compounds are present. This is likely due to the oxidation of the antioxidant compounds, e.g. tocopherols, present in the oil. Removal of the esters according to the process of the invention prior to interesterification would minimize this darkening.

Thus, an improvement in stripping/deodorization or physical refining is gained by utilizing the esterification of antioxidant compounds, e.g. tocopherols, according to the process of the invention prior to a stripping/deodorization or physical refining treatment. Enhanced recovery of the esters of the antioxidant compounds is afforded by stripping/deodorization.

The process(es) of the invention afford protection from oxidation of the tocopherols through the formation of their esters as described herein, maximizing the yield and reducing oxidative and dimerization losses. The process(es) of the invention also provide an improvement in stripping/deodorization in that the amount of energy required to strip the tocopherols and sterols is reduced due to their reduced volatility.

As an example, the third oils can be treated to produce alkyds of triglyceride oils. Such alkyds are prepared by conventional processes known to those of ordinary skill in the art. Examples of alkyds include oxidizing alkyds and urethane alkyds.

Depending on the specific first oil being treated, the second oils can alternatively be treated by adsorptive refining followed by a physical refining step. The adsorptive refining can be conducted by conventional methods known to those of ordinary skill in the art.

Depending on the type of compound used to esterify the antioxidant compounds, the second or third oils can, optionally, be washed with a sufficient amount of water or mild aqueous base to remove excess esterification reagents or by-products of the esterification reactions. It is currently preferred to use a water wash.

In a preferred embodiment of the invention, a process for treating a refined triglyceride oil containing tocopherols is provided comprising (a) contacting the refined triglyceride oil with an effective amount of an acyl halide or reactive carboxylic acid, preferably an acyl halide, under suitable reaction conditions to esterify at least about 90% of the tocopherols to produce a second triglyceride oil containing tocopherol esters; (b) stripping/deodorizing the second triglyceride oil to remove the tocopherol esters and produce a third oil; and (c) recovering the tocopherol esters removed by the stripping/deodorizing. In one aspect of this preferred embodiment, the process further comprises interesterifying the third oil in the presence of a suitable base or acid catalyst to produce a product selected from interesterified oils, or esters or partial esters of fatty acids.

In another preferred embodiment of the invention, a process for treating a refined triglyceride oil containing tocopherols is provided comprising (a) contacting the refined triglyceride oil with an effective amount of an acyl halide or reactive carboxylic acid, preferably an acyl halide, under suitable reaction conditions to esterify at least about 90% of the tocopherols to produce a second triglyceride oil containing tocopherol esters; (b) physical refining the second triglyceride oil to produce a third oil.

EXAMPLES

Example 1

250 grams of refined linseed oil was placed in a 500 ml round bottom flask and fitted with a heating mantle and a magnetic stirrer. Sixteen injections of 25 μL each of acetyl chloride were added drop wise, slowly through a needle hole in the wall of Tygon® tubing (Saint-Gobain Performance Plastics) through which nitrogen gas carried the volatilizing acetyl chloride into the reaction mixture through a gas dispersion tube. The temperature of the reaction was held at 70° C. over the 1.5 hour period of addition. Approx. 15 mL of the product was water washed once with an equal volume of water at room temperature, separated and dried by filtering through a Whatman #4 filter paper. A clear brilliant oil resulted.

80 drops each of the untreated (control) and treated (invention) refined linseed oil were placed in separate 50 mL beakers. Each sample was placed on a hot plate at 70° C. for 8 hours in the open air to accelerate oxidation and test for yellowing. The color of the invention sample remained unchanged and the control sample yellowed significantly as expected. Color was measured using a Hunter Lab Labscan EX colorimeter. L,A,B color: Invention: 9.98, −0.90 and 0.80 (faint yellow); Control: 10.68, −1.14 and 1.69 (deep yellow).

The results of this example demonstrate that the process of the invention using an acyl halide produces oil that has reduced yellowing than the untreated control oil.

Example 2

250 grams of refined linseed oil was placed in a 500 ml round bottom flask and fitted with a heating mantle and magnetic stirrer. The oil was heated to 100° C. and 40 drops of formic acid was added, and the mixture held at 100° C. and allowed to stir for 24 hours.

80 drops each of the untreated (control) and treated (invention) refined linseed oil were placed in separate 50 mL beakers. Each sample was placed on a hot plate at 70° C. for 4 hours in the open air to accelerate oxidation and test for yellowing. The color of the invention sample remained unchanged and the control sample yellowed significantly as expected. Color was measured using a Hunter Lab Labscan EX colorimeter. L,A,B color: Invention: 10.48, −0.51 and 0.11 (faint yellow); Control: 10.04, −0.75, and 0.98 (deep yellow).

The results of this example demonstrate that the process of the invention using a reactive carboxylic acid produces oil that has reduced yellowing than the untreated control oil.

Example 3

250 grams of soybean oil was treated as described in Example 1 above. The Oil Stability Index (OSI) Analysis (American Oil Chemists Society Official Method Cd 12b-92) was run at 110° C. on the resultant product (invention) and on an unreacted control sample. The OSI is an analysis giving the induction time in hours of oils. The induction time is the measure of antioxidant activity, which retards oxidation. The longer the induction time, the greater the antioxidant activity.

The control sample had the greatest antioxidant activity with an OSI of 7.05 hr. The acetyl chloride reacted invention sample had significantly reduced induction time with an OSI of 3.25 hr. The results demonstrate that the process of the invention reduces the drying time of oil compared to the control.

The product of Example 1 (invention) and its control were also analyzed by OSI. Under the conditions of the OSI analysis, the control sample had an OSI of 0.4 hr and the invention sample had an OSI of 0.1 hr. At the temperature of this test both samples rapidly oxidized, but the results were in agreement with the results achieved in the OSI analysis of soybean oil above.

Example 4

250 grams of refined linseed oil was placed in a 500 mL round bottom flask and fitted with a heating mantle and magnetic stirrer. 40 μL of acetic anhydride was added at one time. The acetic anhydride remained as immiscible droplets which did not effectively solubilize. The reaction mixture was heated to 135° C. for 24 hours after which time the droplets disappeared. The resultant product smelled of acetic acid or anhydride following the reaction. 15 mL of product was water washed with 15 mL of water. Sodium chloride (one-half teaspoon) was added to facilitate separation of the water layer which was then separated. The product was filtered through Whatman #4 filter paper to dry.

80 drops each of the product oil (invention) and an untreated refined linseed oil (control) were each placed in 50 mL beakers and heated on a hot plate at 70° C. for 5 hours then set aside at room temperature. After 20 days, the acetic anhydride treated sample (invention) had started to film and was less yellow than the control which was still very fluid and darker yellow. This indicates that use of anhydrides in the process of the invention does work, even though it is currently not the preferred method.

What is claimed is:

1. A process for treating a first oil containing antioxidant compounds selected from tocopherols, tocotrienols, sterols, or mixtures thereof comprising contacting said first oil with an effective amount of at least one compound under suitable reaction conditions to esterify at least about 50% of said antioxidant compounds to produce a second oil containing esters of said antioxidant compounds.

2. The process of claim 1 wherein said first oil is contacted with an acyl halide, said acyl halide being contacted directly with said first oil or formed in situ in said first oil.

3. The process of claim 2 wherein said acyl halide is selected from acyl chloride, acyl bromide, or mixtures thereof.

4. The process of claim 2 wherein said acid halide is represented by the formula:

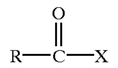

wherein R is selected from $C_1$–$C_{23}$ alkyl, or phenyl, and R is optionally substituted with at least one Cl or Br group; and wherein X is selected from Cl or Br.

5. The process of claim 4 wherein said acyl halide is selected from acetyl chloride, benzoyl chloride, trichloroacetyl chloride, propanoyl chloride, hexanoyl chloride, or mixtures thereof.

6. The process of claim 2 wherein said acyl halide is formed in situ by contacting said first oil with an inorganic acid halide selected from $SOX_2$, $PX_3$ or $PX_5$, said first oil containing an amount of free carboxylic acid sufficient to react with said inorganic acid halide, wherein X is selected from Cl or Br.

7. The process of claim 2 wherein said acyl halide is formed in situ by contacting said first oil with an inorganic acid halide selected from $SOX_2$, $PX_3$ or $PX_5$, and a carboxylic acid, wherein X is selected from Cl or Br.

8. The process of claim 7 wherein said carboxylic acid is a $C_2$ to $C_{24}$ carboxylic acid.

9. The process of claim 1 wherein said first oil is contacted with a reactive carboxylic acid.

10. The process of claim 9 wherein said reactive carboxylic acid is a $C_1$ to $C_6$ aliphatic carboxylic acid.

11. The process of claim 10 wherein said carboxylic acid is selected from formic acid, acetic acid, trichloroacetic acid, or mixtures thereof.

12. The process of claim 1 wherein said first oil is contacted with a carboxylic acid anhydride.

13. The process of claim 12 wherein said anhydride is soluble in said first oil.

14. The process of claim 1 wherein said first oil is a triglyceride based oil.

15. The process of claim 14 wherein said first oil is a triglyceride oil.

16. The process of claim 15 wherein said triglyceride oil is selected from vegetable oils, fish oils, or mixtures thereof.

17. The process of claim 16 wherein said triglyceride oil is selected from linseed oil, menhaden oil, soybean oil, tung oil, oiticica oil, sunflower oil, corn oil, rapeseed oil, cottonseed oil, peanut oil, olive oil, rice bran oil, wheat germ oil, canola oil, hydrogenated and partially hydrogenated oils, palm oil, palm kernel oil, coconut oil, oils from genetically modified seeds, or mixtures thereof.

18. The process of claim 14 wherein said first oil is a modified triglyceride oil.

19. The process of claim 18 wherein said modified triglyceride oil is selected from conjugated oils, blown oils, heat bodied oils, enzyme interesterified oils, mild base catalyzed interesterified oils, high pressure interesterified oils, or chemically modified oils.

20. The process of claim 14 wherein said first oil comprises enzyme, mild base catalyzed or high pressure interesterified compounds selected from monoglycerides, diglycerides, diols, polyols, or mixtures thereof.

21. The process of claim 14 wherein said first oil is selected from a crude oil, a degummed oil, or a refined oil.

22. The process of claim 1 further comprising stripping/deodorizing said second oil.

23. The process of claims 1 or 22 further comprising carbon treating said second oil.

24. The process of claims 1, 22 or 23 further comprising bleaching said second oil.

25. The process of claims 1, 22 or 23 further comprising subjecting said second oil to a further processing step selected from blowing, heat bodying, oxidation, conjugation, epoxidation, hydroformylation, hydroxylation, peroxidation, ozonolysis, chemical modification, interesterification, or complexation.

26. The process of claim 1 wherein said first oil is deodorized prior to esterifying said antioxidant compounds.

27. The process of claim 1 wherein said first oil is carbon treated prior to esterifying said antioxidant compounds.

28. The process of claim 1 wherein said first oil is bleached prior to esterifying said antioxidant compounds.

29. The process of claim 1 further comprising water washing said second oil.

30. The process of claim 1 wherein at least about 75% of said antioxidant compounds are esterified.

31. The process of claim 30 wherein at least about 90% of said antioxidant compounds are esterified.

32. The process of claim 31 wherein at least about 95% of said antioxidant compounds are esterified.

33. The process of claim 1 wherein the ratio of the equivalents of said compound to esterify said antioxidant compounds to the equivalents of hydroxyl groups in said antioxidant compounds is about 1:1 to about 10:1.

34. The process of claim 33 wherein the ratio of the equivalents of said compound to esterify said antioxidant compounds to the equivalents of hydroxyl groups in said antioxidant compounds is about 1.1:1 to about 2:1.

35. The process of claim 1 wherein said esters of said antioxidant compounds comprise esters selected from tocopherol esters, tocotrienol esters, or mixtures thereof.

36. A process for treating a first oil containing antioxidant compounds selected from tocopherols, tocotrienols, sterols, or mixtures thereof comprising:

(a) contacting said first oil with an effective amount of at least one compound under suitable reaction conditions to esterify at least about 50% of said antioxidant compounds to produce a second oil containing esters of said antioxidant compounds; and (b) stripping/deodorizing said second oil to remove said esters of said antioxidant compounds and produce a third oil.

37. The process of claim 36 wherein said first oil is contacted with an acyl halide, said acyl halide being contacted directly with said first oil or formed in situ in said first oil.

38. The process of claim 37 wherein said acyl halide is selected from acyl chloride, acyl bromide, or mixtures thereof.

39. The process of claim 37 wherein said acid halide is represented by the formula:

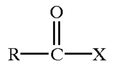

wherein R is selected from $C_1$–$C_{23}$ alkyl, or phenyl, and R is optionally substituted with at least one Cl or Br group; and wherein X is selected from Cl or Br.

40. The process of claim 39 wherein said acyl halide is selected from acetyl chloride, benzoyl chloride, trichloroacetyl chloride, propanoyl chloride, hexanoyl chloride, or mixtures thereof.

41. The process of claim 37 wherein said acyl halide is formed in situ by contacting said first oil with an inorganic acid halide selected from $SOX_2$, $PX_3$ or $PX_5$, said first oil containing an amount of free carboxylic acid sufficient to react with said inorganic acid halide, wherein X is selected from Cl or Br.

42. The process of claim 37 wherein said acyl halide is formed in situ by contacting said first oil with an inorganic acid halide selected from $SOX_2$, $PX_3$ or $PX_5$, and a carboxylic acid, wherein X is selected from Cl or Br.

43. The process of claim 42 wherein said carboxylic acid is a $C_2$ to $C_{24}$ carboxylic acid.

44. The process of claim 36 wherein said first oil is contacted with a reactive carboxylic acid.

45. The process of claim 44 wherein said reactive carboxylic acid is a $C_1$ to $C_6$ aliphatic carboxylic acid.

46. The process of claim 45 wherein said carboxylic acid is selected from formic acid, acetic acid, trichloroacetic acid, or mixtures thereof.

47. The process of claim 36 wherein said first oil is contacted with a carboxylic acid anhydride.

48. The process of claim 47 wherein said anhydride is soluble in said first oil.

49. The process of claim 36 wherein said esters of said antioxidant compounds comprise esters selected from tocopherol esters, tocotrienol esters, or mixtures thereof.

50. The process of claim 36 wherein said second oil is treated by adsorptive refining prior to said stripping/deodorizing.

51. The process of claim 36 further comprising recovering said esters of said antioxidant compounds removed by said stripping/deodorizing.

52. The process of claim 36 further comprising interesterifying said third oil in the presence of a suitable base or acid catalyst to produce an interesterified oil.

53. The process of claim 36 wherein said first oil is a triglyceride based oil.

54. The process of claim 53 wherein said first oil is a triglyceride oil.

55. The process of claim 54 wherein said triglyceride oil is selected from vegetable oils, fish oils, or mixtures thereof.

56. The process of claim 54 wherein said triglyceride oil is selected from linseed oil, menhaden oil, soybean oil, tung oil, oiticica oil, sunflower oil, corn oil, rapeseed oil, cottonseed oil, peanut oil, olive oil, rice bran oil, wheat germ oil, canola oil, hydrogenated and partially hydrogenated oils, palm oil, palm kernel oil, coconut oil, oils from genetically modified seeds, or mixtures thereof.

57. The process of claim 53 wherein said first oil is a modified triglyceride oil.

58. The process of claim 57 wherein said modified triglyceride oil is selected from conjugated oils, blown oils, heat bodied oils, enzyme interesterified oils, mild base catalyzed interesterified oils, high pressure interesterified oils, or chemically modified oils.

59. The process of claim 53 wherein said first oil comprises enzyme, mild base catalyzed or high pressure interesterified compounds selected from monoglycerides, diglycerides, diols, polyols, or mixtures thereof.

60. The process of claim 53 wherein said first oil is a crude oil, a degummed oil, or a refined oil.

61. The process of claim 36 wherein at least about 75% of said antioxidant compounds are esterified.

62. The process of claim 61 wherein at least about 90% of said antioxidant compounds are esterified.

63. The process of claim 62 wherein at least about 95% of said antioxidant compounds are esterified.

64. The process of claim 36 wherein the ratio of the equivalents of said compound to esterify said antioxidant compounds to the equivalents of hydroxyl groups in said antioxidant compounds is about 1:1 to about 10:1.

65. The process of claim 64 wherein the ratio of the equivalents of said compound to esterify said antioxidant compounds to the equivalents of hydroxyl groups in said antioxidant compounds is about 1.1:1 to about 2:1.

66. A product produced by the process of claim 1.

67. A product produced by the process of claim 22.

68. A product produced by the process of claim 23.

69. A product produced by the process of claim 36.

70. A process for treating a refined triglyceride oil containing tocopherols, sterols or mixtures thereof comprising:

(a) contacting said refined triglyceride oil with an effective amount of an acyl halide or reactive carboxylic acid under suitable reaction conditions to esterify at least about 90% of said tocopherols, sterols or mixtures thereof to produce a second triglyceride oil containing tocopherol esters, sterol esters or mixtures thereof;

(b) stripping/deodorizing said second triglyceride oil to remove said tocopherol esters, sterol esters or mixtures thereof and produce a third oil; and (c) recovering said tocopherol esters, sterol esters or mixtures thereof removed by said stripping/deodorizing.

71. The process of claim 70 further comprising interesterifying said third oil in the presence of a suitable base or acid catalyst to produce an interesterified oil.

72. The process of claim 70 wherein said refined triglyceride oil is contacted with an acyl halide.

73. A process for treating a refined triglyceride oil containing tocopherols, sterols or mixtures thereof comprising:

(a) contacting said refined triglyceride oil with an effective amount of an acyl halide or reactive carboxylic acid under suitable reaction conditions to esterify at least about 90% of said tocopherols, sterols or mixtures thereof to produce a second triglyceride oil containing tocopherol esters, sterol esters or mixtures thereof; and (b) physical refining said second triglyceride oil to produce a third oil.

74. The process of claim 73 wherein said refined triglyceride oil is contacted with an acyl halide.

* * * * *